(12) United States Patent
Maycher

(10) Patent No.: US 10,765,497 B2
(45) Date of Patent: Sep. 8, 2020

(54) DENTAL SUCTION DEVICE

(71) Applicant: D.J. Maycher Investments Inc., Vancouver (CA)

(72) Inventor: David John Maycher, Vancouver (CA)

(73) Assignee: MAYCHER HEALTH CARE INNOVATIONS INC., Vancouver, British Columbia (CA)

(*) Notice: Subject to any disclaimer, the term of this patent is extended or adjusted under 35 U.S.C. 154(b) by 0 days.

(21) Appl. No.: 15/328,142

(22) PCT Filed: Jul. 21, 2015

(86) PCT No.: PCT/CA2015/050676
§ 371 (c)(1),
(2) Date: Jan. 23, 2017

(87) PCT Pub. No.: WO2016/011547
PCT Pub. Date: Jan. 28, 2016

(65) Prior Publication Data
US 2017/0216003 A1    Aug. 3, 2017

Related U.S. Application Data

(60) Provisional application No. 62/028,078, filed on Jul. 23, 2014.

(51) Int. Cl.
*A61C 17/08* (2006.01)
*A61M 25/02* (2006.01)
(Continued)

(52) U.S. Cl.
CPC ............ *A61C 17/08* (2019.05); *A61C 15/041* (2013.01); *A61M 1/008* (2013.01); *A61M 25/02* (2013.01);
(Continued)

(58) Field of Classification Search
CPC ..... A61C 17/043; A61C 15/041; A61C 17/04; A61C 17/06; A61C 17/096; A61C 17/10;
(Continued)

(56) References Cited

U.S. PATENT DOCUMENTS 3,049,806 A    8/1962    Cofresi
3,091,856 A *  6/1963    Goldstein ................ A61C 7/00
                                                           433/18
(Continued)

OTHER PUBLICATIONS

Search Report and Written Opinion for PCT Application No. PCT/CA2015/05076, dated Oct. 9, 2015.
(Continued)

*Primary Examiner* — Heidi M Eide
*Assistant Examiner* — Drew S Folgmann
(74) *Attorney, Agent, or Firm* — Gowling WLG (Canada) LLP

(57) ABSTRACT

The present invention relates to a dental suction device for managing fluid in a patient's mouth during a dental procedure. The dental suction device comprises a pliable tube having a first end for connection to a vacuum source and a second end that can be looped to form a suction end for positioning in a patient's mouth. The loop is adjustably secured by a pair of retaining collars positioned a certain distance apart from each other along the second end of the tube and connected together by a tie. The loop, adjusted to accommodate the shape of the patient's mouth, is secured around the terminal end of a row of teeth in the patient's mouth. In this way, the dental suction device can be maintained and operated in the patient's mouth during a dental procedure.

21 Claims, 6 Drawing Sheets

(51) Int. Cl.
    *A61C 15/04* (2006.01)
    *A61M 1/00* (2006.01)
(52) U.S. Cl.
    CPC .................. *A61M 2025/022* (2013.01); *A61M 2025/0253* (2013.01)
(58) Field of Classification Search
    CPC ....... A61C 19/01; A61M 1/008; A61M 25/02; A61M 2025/022; A61M 2025/0253; A61M 2025/0206
    See application file for complete search history.

(56) References Cited

U.S. PATENT DOCUMENTS

| | | | | |
|---|---|---|---|---|
| 4,260,378 | A * | 4/1981 | O'Neil | A61C 17/043 433/93 |
| 8,585,403 | B2 | 11/2013 | Ames | |
| 2009/0126742 | A1 * | 5/2009 | Summer | A61F 5/37 128/848 |
| 2010/0124727 | A1 * | 5/2010 | Shah | A61F 5/05891 433/19 |
| 2012/0237894 | A1 * | 9/2012 | Maycher | A61C 17/043 433/95 |

OTHER PUBLICATIONS

International Preliminary Report on Patentability for corresponding PCT Application No. PCT/CA2015/050676 dated Feb. 2, 2017.

* cited by examiner

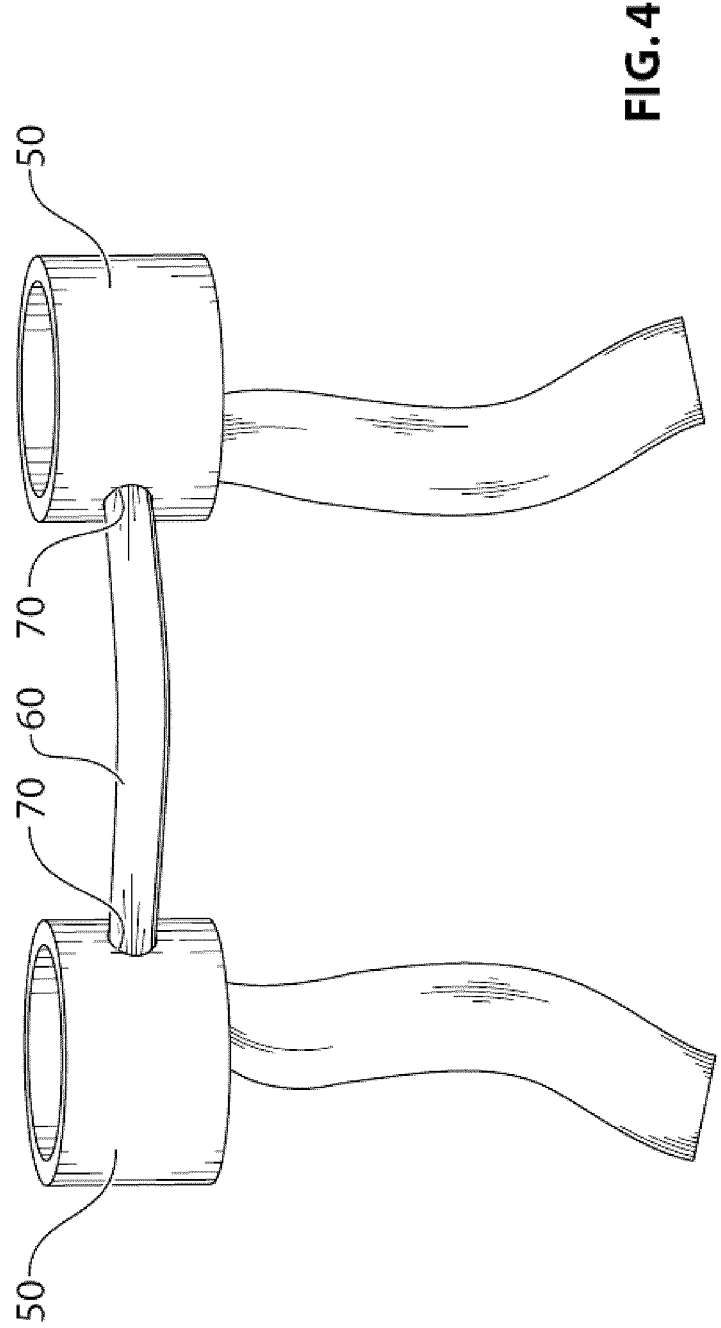

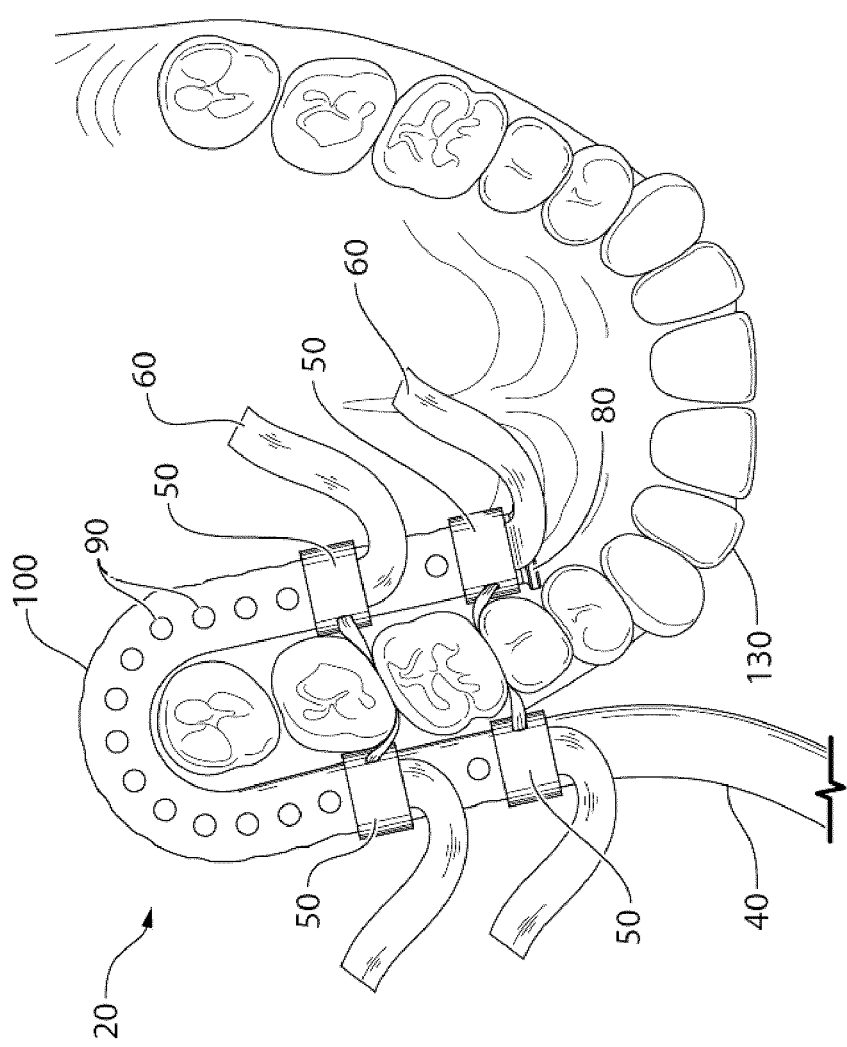

DENTAL SUCTION DEVICE

FIELD OF THE INVENTION

The present invention relates to the field of suction devices and, in particular, to a dental suction device for managing fluid in a patient's mouth during a dental procedure.

BACKGROUND OF THE INVENTION

Dental suction devices, also known as a saliva ejector, moisture evacuator, or suction hose, are used to vacuum saliva and debris in order to maintain a dry and clear operation space in a patient's mouth as well as to ensure patient comfort. Dental suctions most commonly used are characterized by a relatively rigid tubing that is periodically inserted into the patient's mouth by a dental professional as needed during a procedure, or is alternatively hooked onto the side of the patient's mouth for hands-free operation. The insertion of such devices into the patient's mouth can be disruptive to the dental procedure, as well as uncomfortable for the patient who may experience tissue abrasions and bruising.

A variety of suction devices have been developed to address some of these issues. U.S. Patent Publication No. 2004/0197732 describes a suction device that incorporates a clamp for detachably securing the device to a patient's tooth. A suction nozzle is held in position on the clamp which can be further sutured to a suitable point either inside or outside the mouth of the patient for added security.

U.S. Patent Publication No. 2012/0237894 describes a dental apparatus for removing fluid from a patient's mouth during a dental procedure. The apparatus comprises an intraoral tip through which saliva is vacuumed within the mouth of the patient. The intraoral tip can be secured to a tooth by a fastener such that the tip can be continuously fixed inside the patient's mouth throughout the dental procedure.

There remains a continuing need for a convenient, simple, and relatively inexpensive dental suction device that effectively prevents the accumulation of saliva during a dental procedure while being conducive to patient comfort.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The embodiments of the present disclosure relate to a dental suction device. In accordance with one aspect, there is described a dental suction device comprising: a pliable tube having a first end for connection to a vacuum source and a second end for positioning in a patient's mouth, the second end having a plurality of apertures through which fluid is suctioned from the patient's mouth; one or more pairs of retaining collars, wherein each pair of retaining collars comprises a first retaining collar securely positioned at a certain distance apart from a second retaining collar along the second end of the tube; and a tie connecting each pair of retaining collars so as to create a loop at the second end of the tube, wherein the loop can be hooked around the terminal end of a row of teeth and each tie secured between teeth in the row to secure the device in the patient's mouth.

In accordance with another aspect, there is described a dental suction device comprising: a pliable tube having a first end for connection to a vacuum source and a second end for positioning in a patient's mouth, the second end terminating in a flared rim and having a plurality of apertures distributed at the second end through which fluid is suctioned from the patient's mouth; one or more pairs of retaining collars, wherein each pair of retaining collars comprises a first retaining collar securely positioned at a certain distance apart from a second retaining collar along the second end of the tube; and a tie connecting each pair of retaining collars so as to create a loop at the second end of the tube, wherein the loop can be hooked around the terminal end of a row of teeth and each tie secured between teeth in the row to secure the device in the patient's mouth.

In accordance with a further aspect, there is described a system for managing fluid in a patient's mouth during a dental procedure, comprising: a dental suction device according to embodiments of the present disclosure; and a vacuum source for supplying a suction vacuum to the dental suction device; wherein the dental suction device is connected to the vacuum source at the first end of the pliable tube.

According to another aspect, there is described a method for managing fluid in a patient's mouth during a dental procedure, comprising: securing a dental suction device according to embodiments of the present disclosure inside the patient's mouth;

and activating a vacuum source operably connected to the dental suction device to vacuum suction fluid from the patient's mouth during the dental procedure.

BRIEF DESCRIPTION OF THE DRAWINGS

These and other features of the invention will become more apparent in the following detailed description in which reference is made to the appended drawings.

FIG. 4 is a close-up perspective view of a pair of retaining collars and corresponding tie at the suction end of a dental suction device, according to embodiments of the present disclosure;

FIG. 5 is a schematic view of a dental suction device, according to embodiments of the present disclosure, positioned in a patient's mouth.

DETAILED DESCRIPTION OF THE INVENTION

The dental suction device according to the present disclosure provides a convenient, easy to use, means for managing fluid in a patient's mouth during a dental procedure. According to embodiments of the present disclosure, the dental suction device comprises pliable tubing that can be formed to accommodate the shape of the patient's mouth. The pliable tubing is smooth and flexible thereby minimizing the risk of causing abrasion or bruising to the patient when positioned in the patient's mouth.

Furthermore, because the suction device, according to embodiments of the present disclosure, does not require bulky parts or attachments, the device is conducive to patient comfort.

According to embodiments of the present disclosure, the dental suction device is configured to be looped at the suctioning end of the tube for adjustably securing around the terminal end of a row of teeth in the patient's mouth. In this way, the dental suction device can be maintained and operated in the patient's mouth during a dental procedure. Accordingly, in such embodiments, fluid levels in the patient's mouth can be managed without interrupting the dental professional's flow of work. In certain embodiments, the dental suction device can be configured to allow the patient to control the amount of vacuum suction being supplied to the dental suction device. The patient can thereby directly manage fluid levels in their mouth during a dental procedure.

Definitions

Unless defined otherwise, all technical and scientific terms used herein have the same meaning as commonly understood by one of ordinary skill in the art to which this invention belongs.

As used herein, the term "disposable" describes articles that are not intended to be restored or reused and which are intended to be discarded after a single use.

As used herein, the term "rate of fluid removal" refers to the rate at which saliva is being suctioned from a patient's mouth.

As used herein, the term "about" refers to an approximately +/−10% variation from a given value. It is to be understood that such a variation is always included in any given value provided herein, whether or not it is specifically referred to.

Embodiments of the present disclosure will now be described by reference to FIGS. 1 to 6, which show representations of the dental suction device according to the present disclosure.

Figure 1:
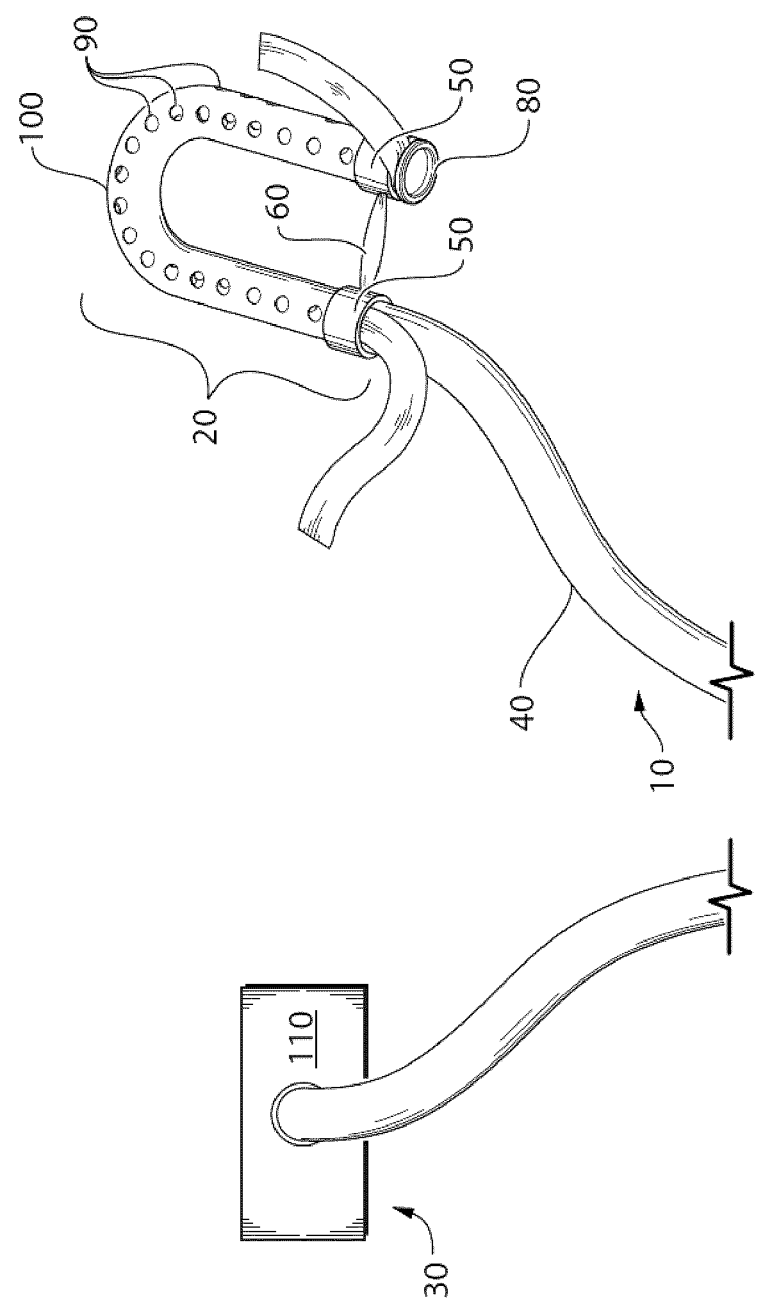
FIG. 1 is a perspective view of a dental suction device having a single tie, according to embodiments of the present disclosure.
Figure 2:
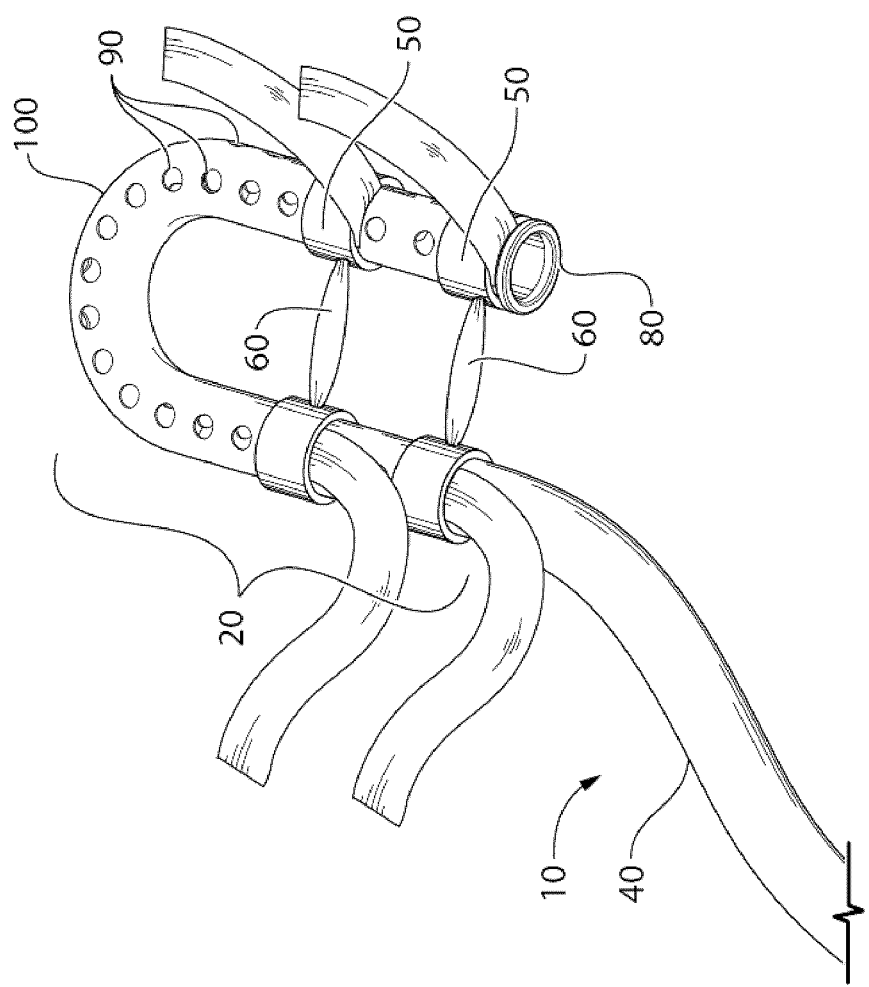
FIG. 2 is a perspective view of a dental suction device having a dual tie, according to embodiments of the present disclosure.

Referring to FIGS. 1 and 2, a dental suction device 10 of the present disclosure comprises a pliable tube 40 adapted at a first end 30 for connection to a vacuum source 110 by any suitable connector known to those skilled in the art. The dental suction device 10 can be adapted for connection to any vacuum system appropriate for use in dental practice. The second end 20 of the pliable tubing 40 operates as the suction end and is for positioning in a patient's mouth. The second end 20, or suction end, comprises a plurality of apertures 90 through which fluid, and according to some embodiments particles of debris, is suctioned from the patient's mouth.

The tube 40 can be made of a semi-rigid polymer including, for example, any suitable plastic, polypropylene, PVC, or polystyrene. The tube 40 is sufficiently rigid to hold its shape yet pliable enough to bend to form the suction end as will be described below. The size of the tube 40 is dependent on the application. For human patients, the tube 40 can have an internal diameter of from about 2 mm to about 10 mm. According to certain embodiments, the dental suction device 10 can be adapted for veterinary applications and, in such embodiments, a larger sized tube 40 can be used. For example, according to such embodiments, the tube 40 can have an internal diameter of greater than about 10 mm. According to further embodiments, the tube 40 can have an internal diameter of up to about 30 mm.

The apertures 90 as shown in FIGS. 1 and 2, are evenly distributed at the second end 20 of the dental suction device 10 to form the suction end. The apertures 90 can be in a repeating pattern over the entire second end 20, or alternatively can partially cover the second end 20. According to other embodiments, the apertures 90 can be unevenly distributed at the second end 20 of the tube 40 (not shown), so long as sufficient suction can be achieved to create the suction end.

Figure 3A:
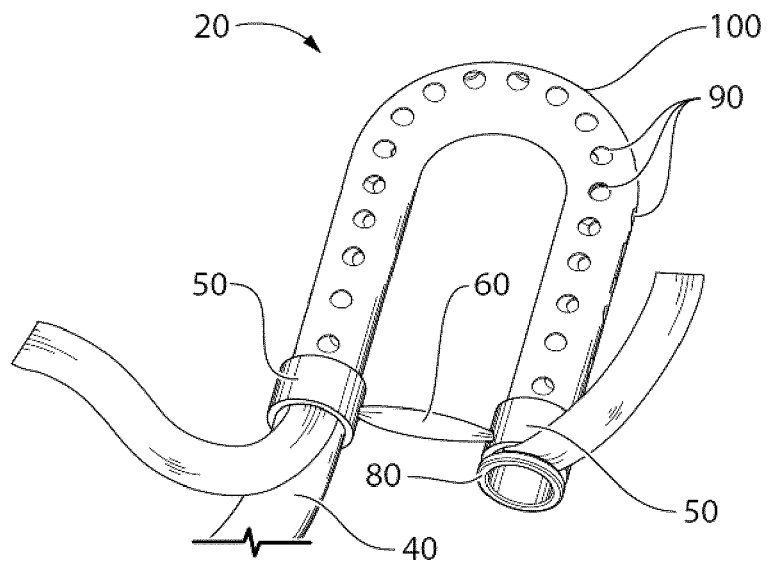
FIG. 3A is a close-up perspective view of the suction end of a dental suction device, according to embodiments of the present disclosure.

As shown in FIG. 3A, the apertures 90 can be circular in shape. According to embodiments of the present disclosure, the circular shaped apertures can range in size and may have a diameter ranging from about 0.25 mm to about 3 mm. According to some embodiments, particularly in applications relating to veterinary dentistry, the diameter of the apertures can exceed 3 mm. According to further embodiment the diameter of the apertures can be up to about 10 mm.

Figure 3B:
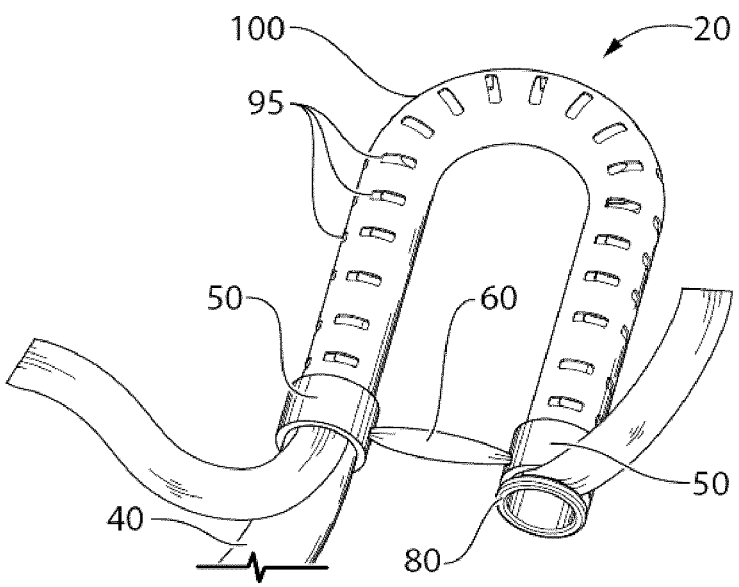
FIG. 3B is a close-up perspective view of the suction end of a dental suction device, according to alternative embodiments of the present disclosure.

According to other embodiments, as shown in FIG. 3B, the apertures 95 can comprise a plurality of slits in the tube 40 so long as sufficient suction can be achieved to create the suction end. Persons of skill in the art will appreciate that the apertures can take any shape and size so long as sufficient suction can be achieved to create the suction end.

The second end 20 of the pliable tube 40 is looped to form the suction end. The length of the second end 20 of the tube 40 must, therefore, be sufficient to allow the second end 20 to form a loop 100. According to certain embodiments, the length of the second end 20 of the tube 40 can range from about 2 cm to about 20 cm, to form a loop 100 of from about 1 cm to about 10 cm, depending on the size of the patient's mouth. According to some embodiments, particularly in applications relating to veterinary dentistry, the length of the second end 20 of the tube 40 can exceed 20 cm, to form a loop 100 exceeding about 10 cm. According to further embodiments, the length of the second end 20 of the tube 40 can be up to about 40 cm, to form a loop 100 of up to about 20 cm.

The loop 100 can be adjusted to any desired size to accommodate a wide range of patients. For example, the loop 100 can be made larger for adults and smaller for children. It is also contemplated that the dental suction device 10 can be used in veterinary dentistry. Accordingly, the loop 100 can further be adjusted to accommodate animals of various sizes. The size and shape of the loop 100 is secured by a pair of retaining collars 50 connected together by a tie 60. Each retaining collar 50 is positioned along the second end 20 of the tube 40 at a certain distance apart from each other. By increasing the distance between the pair of retaining collars 50, the size of the loop 100 can be enlarged. By the same token, by decreasing the distance between the pair of retaining collars 50, the size of the loop 100 can be reduced.

Each retaining collar 50 is sized to fit securely to the outside of the tube 40 in order to maintain the size and shape of the loop 100 forming the suction end, without the risk of slipping during operation. According to some embodiments, the second end 20 of the tube 40 terminates in a flared rim 80 to prevent a retaining collar 50 positioned at the terminal end of the second end 20 from being dislodged off the tube 40. According to certain embodiments, the retaining collars 50 have a diameter large enough to be threadably positioned onto the tube 40 and small enough to be retained by the flared rim 80 at the terminal end of the second end 20 of the tube 40.

According to certain embodiments, the retaining collar 50 and the pliable tube 40 can be made of a semi-rigid polymer including, for example, any suitable plastic, polypropylene, PVC, and polystyrene. In this way, the retaining collar 50 and the tube 40 may have resilient properties and a tackiness in surface tension to further ensure a secure fit. According to certain embodiments, the materials are tolerant to multiple sterilization using methods typically found in dental practice, to allow the dental suction device 10 to be reused. In other embodiments, the dental suction device 10 is for disposable or single use.

Each pair of retaining collars 50 is connected together by a tie 60. When positioned along the tube 40 at the desired distance apart, the pliable tube 40 is bent to connect the pair of retaining collars 50 with the tie 60 and secure the formed loop 100 at the second end 20. According to embodiments of the present disclosure, the tie 60 can be of any suitable material. For example, the tie 60 can be dental floss. According to certain embodiments, the tie 60 can be made of an elastic material. In some embodiments, the elastic material can be latex or non-latex rubber.

The tie 60 is adjustably connected to the pair of retaining collars 50 to allow the loop 100 to be tightened and loosened as needed. According to certain embodiments, and as clearly shown in FIG. 4, each retaining collar 50 in a pair can comprise a hole 70 through which one end of the tie 60 is respectively threaded to allow each end of the tie 60 to be tightly caught between the interior of the respective retaining collar 50 and the exterior of the tube 40. In this way, the tie 60 connects the pair of retaining collars 50 such that pulling a free end of the tie 60 causes shortening of the connection between the respective retaining collars 50 in the pair and tightening of the loop 100. Similarly, releasing the length of the tie 60 between the retaining collars 50 lengthens the connection between the collars 50 causing loosening of the loop 100.

According to embodiments of the present disclosure, as shown in FIG. 5, the loop 100 forming the suction end of the dental suction device 10 can be adjusted to a suitable size and shape to be hooked around the terminal end of a row of the patient's teeth 130. Once positioned, the loop 100 can be tightened by pulling the free end of each tie 60 and then securing the connecting parts of each tie 60 between adjacent teeth in the row 130. In this way, the device 10 is securely positioned in the patient's mouth for removing fluid from the patient's mouth. According to embodiments, the dental suction device 10 is compact and unobtrusive in the tight operating space of a patient's mouth. The dental suction device does not require bulky clamps or fasteners to secure the device in position in the patient's mouth, accordingly, the suction device 10 of the present disclosure can remain in the patient's mouth during a dental procedure without disruption to the dental professional.

The dental suction device 10, as shown in FIG. 5, can be secured to the patient's teeth 130 by two pairs of retaining collars 50 connected between teeth by a respective tie 60. Further embodiments of the dental suction device 10 can include a single pair of retaining collars 50 (FIG. 1), three pairs of retaining collars 50, or more depending on the size of the patient's mouth, the type of dental procedure being carried out, and the location that the vacuum suction is needed in the mouth.

Figure 6:
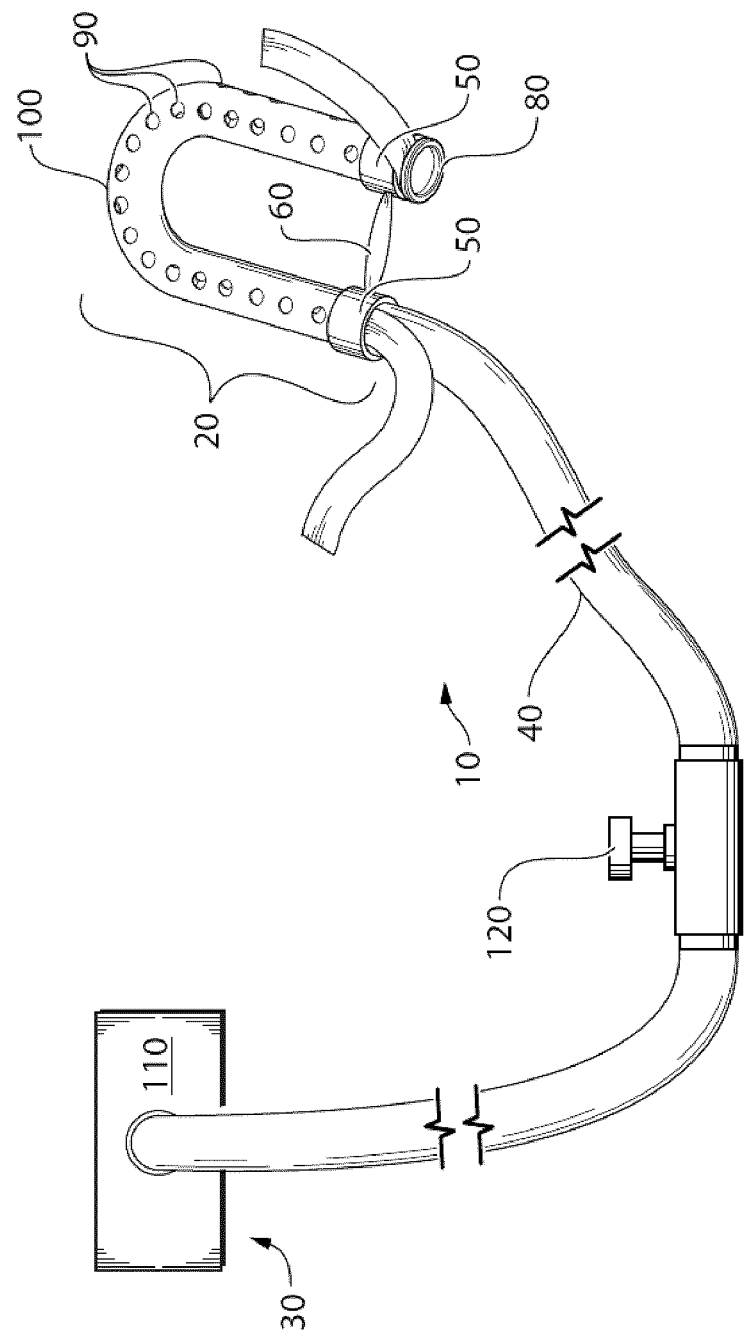
FIG. 6 is a perspective view of a dental suction device adapted for patient control, according to embodiments of the present disclosure.

The dental suction device 10, according to certain embodiments, can be adapted to be directly controlled by the patient during a dental procedure. Referring to FIG. 6, such embodiments can further include a valve 120 located on the tube 40 between the first 30 and second 20 ends. The valve 120 is configured to modulate the rate of fluid removal from the patient's mouth by opening and closing, or partially obstructing, the passageway through the tube 40. In one embodiment, the valve 120 has a plurality of operating positions: in a closed position, no flow passes through the valve 120, in a partially open position, some flow passes through the valve 120 and in an open position, a maximum flow passes through the valve 120. According to certain embodiments, the valve 120 can be movable between the operating positions by a flow control switch that is operable by the patient. According to such embodiments, the valve 120 may be operable by one hand of the patient. The flow control switch is in communication with the valve 120 and enables the patient to control the rate of fluid removal from their mouth during a dental procedure by selecting the desired operating position of the valve 120.

During a dental procedure, the operating positions of the valve 120 can regulate the rate of fluid removal from the patient's mouth. For example, the valve 120 may be set in a partially open position to allow a pre-determined amount of flow to pass through the valve 120. In alternative embodiments, the operating positions of the valve 120 may be continuous between the closed position and the open position so that any amount of flow may be allowed to pass through the valve 120.

In one embodiment, the flow control switch can be a mechanical switch that physically moves the valve 120 between the plurality of operating positions. In one aspect, the mechanical switch is mounted on the tube 40 and applies pressure directly to the tube 40 adjusting the amount of flow through the tube 40. Mechanical flow control switches are well known in the art and therefore will not be described further here. In another embodiment, the flow control switch can be an electrical switch that actuates the valve 120. The electrical switch may include "up" and "down" buttons that actuate the valve 120 between the open and closed positions in increments having a pre-determined size. Electrical flow control switches are well known in the art and therefore will not be described further here.

The simple design of the dental suction device 10 according to embodiments described herein make the device 10 amenable to operate with existing dental vacuum systems. According to certain embodiments, therefore, a system for managing fluid in a patient's mouth during a dental procedure comprises the dental suction device 10 described herein in combination with a vacuum source 110 for supplying a suction vacuum to the dental suction device 10.

To operate the dental suction device 10, according to embodiments of the present disclosure, the suction end formed at the second end 20 of the dental device 10 is placed inside a patient's mouth. Specifically, the loop 100 forming the suction end is secured within the mouth by adjusting the size and shape of the loop 100 to securely hook around the terminal end of a row of the patient's teeth 130. The modular nature of the device 10 further allows the dental professional to adjust the size and shape of the loop 100 to suit the particular patient. For example, pairs of retaining collars 50 can be added or removed as needed to. According to certain embodiments, more than one device 10 can be positioned and operated in a patient's mouth simultaneously. For example, a device 10 can be secured to the terminal end of either or both sides of a patient's upper and/or lower row of teeth 130.

Once the second suction end 20 of the device 10 is secured in the patient's mouth, the first end 30 of the tube 40 extends from the patient's mouth and across the patient's body to connect to the vacuum source 110. According to one embodiment, the vacuum source 110 is turned on during a dental procedure at a suction pressure sufficient to effectively remove fluid from the patient's mouth at a low rate of fluid removal, more specifically at a rate of fluid removal about the salivary flow rate of the patient. Fluid within a patient's mouth flows into the tube 40 through the apertures 90 and is evacuated by standard dental waste practices. In the event an aperture 90 becomes blocked, the plurality of other apertures 90 distributed over the second end 20 can compensate for the blockage and maintain effective operation.

According to certain embodiments, the patient can directly control the rate of fluid removal by manipulating the valve 120. The patient may operate the valve 120 to either increase or decrease the rate of fluid removal as desired according to their comfort. The rate of fluid removal from a patient's mouth is generally at a low rate of fluid removal so that over-drying of the patient's mouth does not occur. More desirably, the rate of fluid removal is about equivalent to the salivary flow rate. Typical salivary flow rates range from between about 0.1 mL/minute and about 0.6 mL/minute, however, a person skilled in the art would understand that salivary flow rates vary between patients.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The invention claimed is:

1. A dental suction device comprising:
   a pliable semi-rigid tube having a first end for connection to a vacuum source and a second end adjustably bendable around a terminal end of a row of teeth in a patient's mouth to form a loop accommodating a shape of the patient's mouth, the second end having a plurality of apertures through which fluid is suctioned from the patient's mouth;
   one or more spaced-apart pairs of resilient retaining collars, wherein each of the one or more pairs of resilient retaining collars is spaced apart at a certain distance along the second end of the tube and engaged therewith; and a pliable tie;
   wherein each of the one or more pairs of resilient retaining collars is provided with a hole therethrough to threadably receive therethrough the pliable tie for interconnecting a pair of the resilient retaining collars whereby the pliable tie may be secured in an interproximal space between two teeth at the terminal end of the row of teeth to thereby secure the looped second end of the device in the patient's mouth.

2. The dental suction device according to claim 1, wherein the second end of the pliable tube terminates in a flared rim.

3. The dental suction device according to claim 1, wherein the tie is adjustably connected to the pair of retaining collars to allow tightening and loosening of the second end of the tube around the row of teeth.

4. The dental suction device according to claim 1, wherein each retaining collar in the pair allows for each end of the tie to be tightly caught between the interior of the respective retaining collar and the exterior of the tube, wherein the tie connects the pair of retaining collars such that pulling or releasing a free end of the tie causes shortening or lengthening of the connection between the respective retaining collars in the pair, respectively.

5. The dental suction device according to claim 1, wherein the tie is dental floss.

6. The dental suction device according to claim 1, wherein the tie is an elastic material.

7. The dental suction device according to claim 6, wherein the elastic material is latex or non-latex rubber.

8. The dental suction device according to claim 1, wherein the retaining collars have a diameter large enough to be threadably positioned onto the tube and small enough to be retained by a flared rim on the second end of the tube.

9. The dental suction device according to claim 1, wherein the one or more spaced-apart pairs of resilient retaining collars comprises a single pair of retaining collars.

10. The dental suction device according to claim 1, wherein the one or more spaced-apart pairs of resilient retaining collars comprises two pairs of retaining collars.

11. The dental suction device according to claim 1, wherein the plurality of apertures at the second end of the tube are circular in shape.

12. The dental suction device according to claim 11, wherein the diameter of the apertures is from 0.25 mm to 3 mm.

13. The dental suction device according to claim 1, wherein the plurality of apertures at the second end of the tube are slits.

14. The dental suction device according to claim 1, wherein the apertures are evenly distributed at the second end of the tube.

15. The dental suction device according to claim 1, wherein the apertures are unevenly distributed at the second end of the tube.

16. The dental suction device according to claim 1, wherein the length of the second end of the tube is from 2 cm to 20 cm to form a loop from about 1 cm to 10 cm.

17. The dental suction device according to claim 1, wherein the tube has an internal diameter of from 2 mm to 10 mm.

18. The dental suction device according to claim 1, further comprising a valve for modulating the rate of fluid removal from the patient's mouth.

19. The dental suction device according to claim 18, wherein the valve is located between the first and second end of the pliable tube.

20. The dental suction device according to claim 18, wherein the valve has a plurality of operating positions and is moveable between said operating positions.

21. The dental suction device according to claim 18, wherein the valve is operable by the patient.

* * * * *